US008367864B2

(12) United States Patent
Moffett et al.

(10) Patent No.: US 8,367,864 B2
(45) Date of Patent: Feb. 5, 2013

(54) DIMERIC DOUBLE METAL SALTS OF (−)-HYDROXYCITRIC ACID, METHODS OF MAKING AND USES OF SAME

(75) Inventors: Alex Moffett, Chatsworth, CA (US); Parag Shah, Jayanagar (IN)

(73) Assignee: Glykon Technologies Group, LLC, Las Vegas, NV (US)

( * ) Notice: Subject to any disclaimer, the term of this patent is extended or adjusted under 35 U.S.C. 154(b) by 434 days.

(21) Appl. No.: 12/694,828

(22) Filed: Jan. 27, 2010

(65) Prior Publication Data

US 2011/0003896 A1 Jan. 6, 2011

Related U.S. Application Data

(63) Continuation of application No. 11/611,817, filed on Dec. 15, 2006, now abandoned.

(51) Int. Cl.
 *C07C 51/09* (2006.01)
(52) U.S. Cl. ......................................... 562/512; 562/590
(58) Field of Classification Search ........................ None
See application file for complete search history.

(56) References Cited

U.S. PATENT DOCUMENTS

| | | | |
|---|---|---|---|
| 6,160,172 | A | 12/2000 | Balasubramanyam et al. |
| 6,875,891 | B2 | 4/2005 | Gokaraju et al. |
| 7,015,250 | B2 | 3/2006 | Clouatre et al. |
| 7,507,421 | B2 | 3/2009 | Bhaskaran et al. |
| 2003/0207942 | A1 | 11/2003 | Bhaskaran et al. |
| 2006/0240074 | A1 | 10/2006 | Gokaraju et al. |
| 2007/0092461 | A1 | 4/2007 | Gupta |

FOREIGN PATENT DOCUMENTS

WO WO 2005/099679 10/2005

OTHER PUBLICATIONS

Glusker, et al., "The Structure and Absolute Configuration of the Calcium Salt of Garcinia Acid, the Lactone of (−)-Hydroxycitric Acid", *Acta Cryst.*, 1971, B27, pp. 1284-1293.
Glusker, et al., "The Structure and Absolute Configuration of the Calcium Salt of Hibiscus Acid, the Lactone of (+)-allo-Hydroxycitric Acid", *Acta Cryst.*, 1972, B28, pp. 2499-2505.
PCT International Search Report—(PCT/US07/11231) Date of Mailing Dec. 27, 2007.

*Primary Examiner* — Yevegeny Valenrod
(74) *Attorney, Agent, or Firm* — Foley & Lardner LLP; Michel Morency

(57) ABSTRACT

The present invention relates to soluble dimeric double metal salt compositions of (−)-hydroxycitric acid ("HCA"), as well as methods for making and using the same. The invention provides dimeric double metal salts of group IA and IIA of HCA (hereinafter, "DDM-HCAs"). The present invention provides methods to make DDM-HCAs of the invention which can be employed to alter the polar/ionic qualities of HCA salts and derivatives to improve solubility of HCA compositions. DDM-HCAs of the invention are soluble HCA-containing compositions useful as dietary supplements and suitable for manipulations under those conditions necessary for tabletting, encapsulation, and the production of dry powders, particularly for use as a beverage premix. Methods of use of the composition include treatment for suppression of appetite, for weight loss, for an increase in the rate of fat metabolism, for reduction in blood lipids and postprandial lipemia, and to increase the plasma level of (−)-hydroxycitric acid.

7 Claims, 1 Drawing Sheet

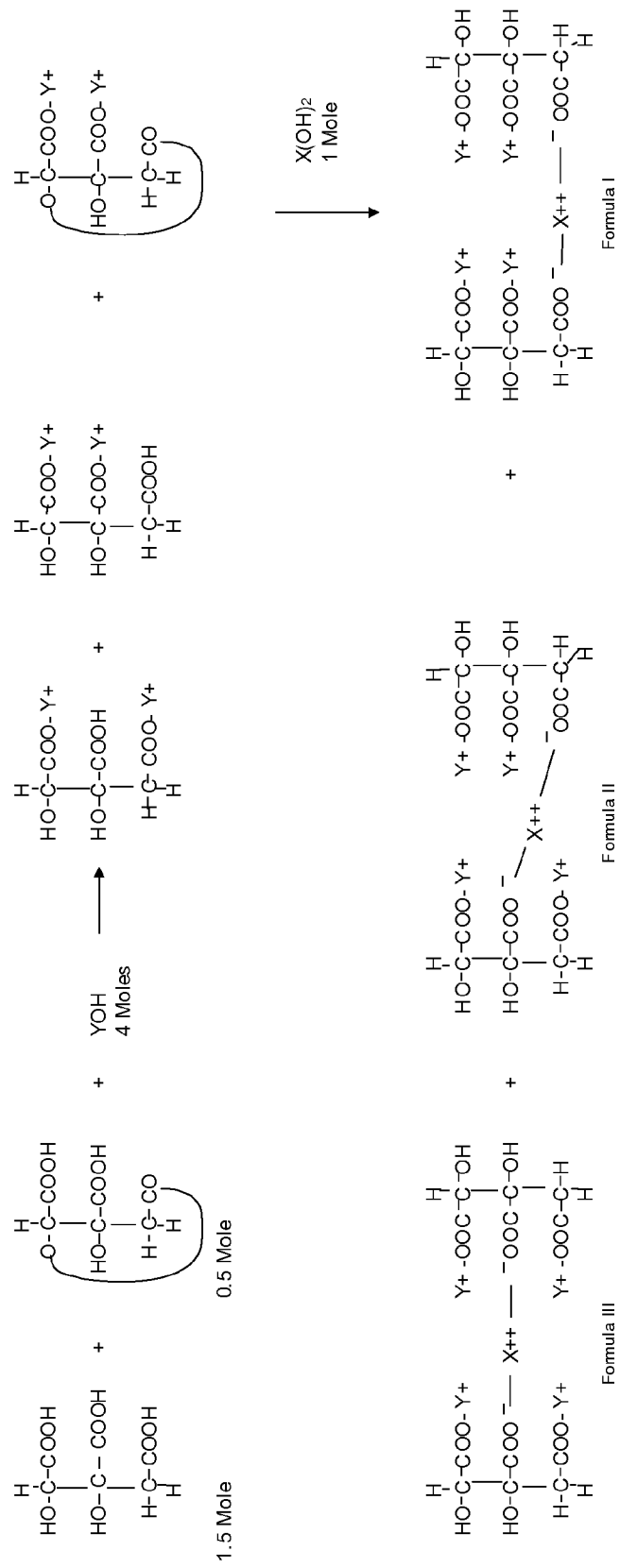

DIMERIC DOUBLE METAL SALTS OF (−)-HYDROXYCITRIC ACID, METHODS OF MAKING AND USES OF SAME

CROSS REFERENCE TO RELATED APPLICATIONS

This application is a continuation application of U.S. application Ser. No. 11/611,817, filed Dec. 15, 2006. The entire teachings of the above application is incorporated herein by reference.

FIELD OF THE INVENTION

The present invention relates to dimeric double metal salt compositions of (−)-hydroxycitric acid ("HCA"), as well as methods for making and using the same.

BACKGROUND OF THE INVENTION

HCA is a naturally-occurring derivative of citric acid found in the fruit of members of the plant genus *Garcinia*. Free HCA, calcium, magnesium and potassium salts of HCA, and poorly characterized mixtures of two or more of these minerals have been sold in the American market, the calcium- and sodium HCA salts since 1994. Most of the commercial preparations of HCA sold to date consist of calcium salts of varying degrees of purity or, more recently, poorly characterized mixtures of calcium HCA and potassium HCA salts.

HCA can affect the metabolism of mammals, including humans. HCA, as well as several synthetic derivatives of citric acid, can inhibit the production of fatty acids from carbohydrates, suppress appetite, and inhibit weight gain (Sullivan et al., American Journal of Clinical Nutrition 1977; 30: 767). Numerous other benefits have been attributed to the use of HCA, including, for example, an increase in the metabolism of fat stores for energy and an increase in thermogenesis (the metabolism of energy sources to produce body heat in an otherwise wasteful cycle).

The therapeutic use of HCA salts has been limited, however, by their poor absorption and chemical instability at acidic pH, e.g., inactivation of HCA salts via lactonization upon exposure to the acidic milieu of the mammalian gut. HCA in either its favored form for biological availability, as the potassium HCA salt, or in its secondarily favored form for biological availability, as sodium HCA salt, is extremely hygroscopic. As such, HCA in its more biologically active forms can be only maintained as a powder under well-controlled dry conditions. There remains a need for soluble HCA-containing compositions suitable for inclusion in dry delivery formats, liquid delivery, and in controlled-release vehicles.

SUMMARY OF THE INVENTION

The invention provides a dimeric, double metal salt of group IA and group IIA of HCA (hereinafter, "DDM-HCA") of general formulas Formula I; Formula II; or Formula III, or any mixture thereof, as given below in Table 1), where X is IIA group metal: such as Be, Mg, Ca, Sr, Ba, or Ra; where Y is IA group metal: such as Li, Na, K, Rb, Cs, or Fr; and where the relative molar ratio of IIA group metal to IA group metal is from at least about 1.0:3.5 to at least about 1.0:4.5. In one embodiment, the DDM-HCA is a composition where (i) X is magnesium metal; (ii) Y is potassium metal; and (iii) the relative molar ratio of magnesium metal to potassium metal is from at least about 1.0:3.5 to at least about 1.0:4.5.

TABLE 1

HCA Formulas I, II, and III

Formula I

HO—C(H)—COO—Y+   Y+—OOC—C(H)—OH
HO—C(H)—COO—Y+   Y+—OOC—C(H)—OH
H—C(H)—COO⁻—X++——⁻OOC—C(H)\\H

Formula II

HO—C(H)—COO—Y+        Y+—OOC—C(H)—OH
HO—C(H)—COO⁻\\         Y+—OOC—C(H)—OH
                X++
H—C(H)—COO—Y+         ⁻OOC—C(H)\\H

Formula III

HO—C(H)—COO—Y+    Y+—OOC—C(H)—OH
HO—C(H)—COO⁻——X++——⁻OOC—C(H)—OH
H—C(H)—COO—Y+    Y+—OOC—C(H)—H

In one aspect, the invention provides a process of preparing DDM-HCA of general formula Formula I; Formula II; or Formula III, or any mixture thereof, as described and depicted above, comprising the steps of: (a) preparing a liquid HCA/lactone concentrate mixture; (b) partially neutralizing 2 molar equivalents of the liquid HCA/lactone concentrate mixture with 4 molar equivalents of a group IA metal hydroxide under conditions wherein the reaction temperature is maintained from at least about 27° C. to at least about 33° C. to yield a partially neutralized liquid HCA/lactone concentrate mixture; (c) reacting the partially neutralized liquid HCA/lactone concentrate mixture of step b with one (1) molar equivalent of a IIA metal hydroxide to yield a fully neutralized liquid HCA/lactone concentrate mixture; (d) hydrolyzing the lactone component of the fully neutralized liquid HCA/lactone concentrate mixture of step c by heating the mixture to at least about 60° C. until the pH of the mixture is stable from about pH 8.8 to about pH 9.2 to yield a HCA dimeric double metal salt solution; and (e) isolating the dimeric, double metal salts of group IA and group IIA of HCA from the HCA dimeric, double metal salt solution of step d.

In one embodiment, a liquid HCA/lactone concentrate mixture is derived from *Garcinia* is derived by extracting a (−)-hydroxycitric acid/lactone concentrate mixture from dried *Garcinia* rind. The process of preparing the DDM-HCA, the preparation of the liquid HCA/lactone concentrate mixture further comprises: (a) extracting HCA from a dried *Garcinia* rind with demineralized (DM) water in an extractor for at least about 6 hours to yield a first *Garcinia* extract and a once-extracted *Garcinia* rind; (b) filtering the first *Garcinia* extract of step a; (c) extracting the once-extracted *Garcinia* rind of step a with DM water in an extractor for at least about 6 hours to yield a second *Garcinia* extract and a twice-extracted *Garcinia* rind; (d) filtering the second *Garcinia* extract of step c; (e) extracting the twice-extracted *Garcinia* of step c with DM water in an extractor for at least about 6 hours to yield a third *Garcinia* extract and a three-times-extracted *Garcinia* rind; (f) filtering the third *Garcinia* extract of step e; (g) extracting the three-times-extracted *Garcinia* rind of step e with DM water in an extractor for at least about 6 h yield a fourth *Garcinia* extract and a four-times-extracted *Garcinia* rind; (h) filtering the fourth *Garcinia* extract of step f; (i) combining the filtered *Garcinia* extracts from step b, step d, step f and step h to yield a combined *Garcinia* mixture; (j) homogenizing the combined *Garcinia* extract mixture; (k) loading the homogenized *Garcinia* extract mixture of step j onto an anion exchange column for adsorption of the HCA onto the anion exchange column for adsorption of the HCA onto the anion exchange column; (l) eluting the HCA from the anion exchange column with sodium hydroxide solution to yield an anion exchange purified HCA sodium salt solution; (m) loading the purified HCA sodium salt solution of step l onto a cation exchange column for collection of free HCA as a free acid in a cation exchange purified HCA solution; (n) bleaching the cation exchange purified HCA solution of step m by mixing the cation exchange purified HCA solution with activated charcoal for about 1 hour at 80° C. to yield a bleached HCA solution; (o) filtering the bleached HCA solution; (p) cooling the bleached HCA solution to room temperature (p); filtering the bleached HCA solution; (q) loading the bleached HCA solution of step p onto a cation exchange column to reduce the cation concentration of the bleached HCA solution; (r) loading the bleached HCA solution of step p onto an anion exchange column to reduce the chloride concentration of the bleached HCA solution to yield a HCA concentrate with at least about 1.0 percent weight HCA concentration; and (s) aging the HCA concentrate of step q to yield the liquid HCA/lactone concentrate mixture; where wherein the HCA lactone is present at a concentration of least about 20% weight percent of the total weight of the liquid HCA/lactone concentrate mixture of the liquid HON lactone concentrate mixture.

In one embodiment of the process of preparing the DDM-HCA, the HCA/lactone concentrate mixture is partially neutralized, 2 molar equivalents of the liquid HCA/lactone concentrate mixture with 4 molar equivalents of a group IA metal hydroxide. The group IA metal hydroxide solution is slowly added with mixing to the liquid HCA/lactone concentrate mixture under conditions wherein the reaction temperature is maintained from at least about 27° C. to at least about 33° C. to yield a partially neutralized liquid HCA/lactone concentrate mixture. Group IA metal hydroxides useful in the preparation of DDM-HCA include, but are not limited to, e.g., LiOH; NaOH; KOH; RbOH; CsOH; and FrOH. In one embodiment, the HCA/lactone concentrate mixture is maintained at least about 30° C. to yield a partially neutralized liquid HCA/lactone concentrate mixture. After partial neutralization with group IA metal hydroxide, the neutralized liquid HCA/lactone concentrate mixture slowly reacted with mixing with one (1) molar equivalent of a IIA metal hydroxide to yield a fully neutralized liquid HCA/lactone concentrate mixture. Group IIA metal hydroxides useful in the preparation of DDM-HCA include, e.g., $Be(OH)_2$; $Mg(OH)_2$; $Ca(OH)_2$; $Sr(OH)_2$; $Ba(OH)_2$; and $Ra(OH)_2$. The fully neutralized liquid HCA/lactone concentrate mixture is then heated to at least about 60° C. until the pH of the mixture is stable to yield a stabilized DDM-HCA-containing mixture. In one embodiment, the pH of the HCA/lactone concentrate mixture is stabilized in a range from about pH 8.8 to about pH 9.2. The DDM-HCAs are then isolated from the stabilized DDM-HCA-containing mixture by any suitable separation or processing technique. In one embodiment, the DDM-HCAs are isolated from the stabilized DDM-HCA-containing solution by concentrating the stabilized DDM-HCA-containing solution to at least about 25% weight total solids to yield a concentrated DDM-HCA-containing solution. The concentrated DDM-HCA-containing solution is filtered and the DDM-HCA-containing filtrate is dried. In one embodiment, DDM-HCA-containing is dried using spray drying technique.

In another embodiment of the process of preparing the DDM-HCA, isolation of the DDM-HCA salt(s) from the DDM-HCA solution of step d further comprises: (a) concentrating the HCA dimeric, double metal salt solution to at least about 25% weight percent total solids to yield a concentrated HCA dimeric, double metal salt solution; (b) filtering the concentrated HCA dimeric, double metal salt solution of step a to yield a filtrate; and (c) drying the filtrate of step b. In another embodiment of the process of preparing the DDM-HCA, the filtrate of step b is dried by spray drying. In another embodiment of the process of preparing the DDM-HCA, the group IA metal hydroxide is selected from LiOH; NaOH; KOH; RbOH; CsOH; or FrOH. In another embodiment of the process of preparing the DDM-HCA, the group IIA metal hydroxide is selected from: $Be(OH)_2$; $Mg(OH)_2$; $Ca(OH)_2$; $Sr(OH)_2$; $Ba(OH)_2$; or $Ra(OH)_2$.

In another aspect, the DDM-HCA composition is formulated in a dry delivery system. In one embodiment, the dry delivery system is selected from: a tablet; dry powder; or dry meal replacement mixture.

In another aspect, the DDM-HCA is formulated in a liquid delivery system. In one embodiment, the liquid delivery system is selected from: a capsule; caplet; or beverage.

In another aspect, the DDM-HCA is formulated in a controlled-release system. In another embodiment, the controlled-release system is selected from: a tablet; caplet; or capsule.

In another aspect, the invention provides a pharmaceutical composition containing a DDM-HCA and a pharmaceutically-acceptable carrier.

In another aspect, the invention provided a method of suppressing the appetite in a subject, by administering to a subject in which appetite suppression is desired a DDM-HCA in amount sufficient to suppress the appetite in the subject.

In another aspect, the invention provides a method of reducing the cytoplasmic citrate lyase activity in a subject by administering to a subject in which reducing cytoplasmic citrate lyase activity is desired a DDM-HCA in an amount sufficient to reduce the citrate lyase activity.

In another aspect, the invention provides a method of increasing the fat metabolism in a subject by administering to a subject in which increased fat metabolism is desired a DDM-HCA in an amount sufficient to increase fat metabolism.

In another aspect, the invention provides a method of inducing weight-loss in a subject, by administering to a subject in which weight-loss is desired a DDM-HCA in an amount sufficient to induce weight-loss.

In another aspect, the invention provides a method of reducing blood lipids and postprandial lipemia in a subject by administering to a subject in which reduced blood lipids and postprandial lipemia is desired a DDM-HCA as described above in an amount sufficient to reduce blood lipids and postprandial lipemia.

In another aspect, the invention provides a method of modulating the level of HCA (generally by increasing it) in the plasma of a subject by administering to the subject in which modulation of the level of HCA in the plasma of a subject is desired, an amount of composition comprising a one or more DDM-HCAs sufficient to modulate the level HCA in the plasma. In one embodiment of the method, the rate of appearance of HCA in the plasma of the subject treated with one or more DDM-HCA increases the plasma level significantly above a control level. The control level may be represented by the plasma HCA level prior to treatment, or the level of HCA in an untreated-, or placebo treated control subject. The increase in plasma level of HCA following treatment with a composition comprising one or more DDM-HCAs is due to influx from the gut, the HCA's crossing the lining of the gut and being absorbed by the local capillaries, and thereby entering the blood of the circulatory system.

BRIEF DESCRIPTION OF THE DRAWINGS

FIG. 1 is a schematic diagram detailing the process of some embodiments of the dimeric double metal salt hydroxycitric acid compositions (DDM-HCAs) of the invention.

DETAILED DESCRIPTION OF THE INVENTION

I. Conventions and Terms

A "subject," as used herein, is preferably a mammal, such as a human, but can also be a non-human animal, e.g., domestic animals (e.g., dogs, cats and the like), farm animals (e.g., cows, sheep, pigs, horses and the like), or laboratory animals (e.g., rats, mice, guinea pigs and the like).

An "effective amount" of an DDM-HCA-containing composition of the invention, as used herein, is a quantity sufficient to achieve a desired therapeutic and/or prophylactic effect, for example, an amount which results in the prevention of or a decrease in the symptoms associated with a disease, disorder or condition that is being treated, e.g., obesity, weight gain, hunger, hyperlipemia, postprandial lipemia. The amount of an DDM-HCA-containing composition of the invention administered to the subject will depend on the type and severity of the disease, disorder or condition, and on the characteristics of the individual, such as general health, age, sex, body weight and tolerance to drugs. It will also depend on the degree, severity and type of disease. The skilled artisan will be able to determine appropriate dosages depending on these and other factors.

It is advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by- and directly dependent on the unique characteristics of the dietary supplement, the particular therapeutic effect to be achieved, and the limitations inherent in the art of compounding such an active compound for the treatment of individuals. The pharmaceutical compositions can be included in a container, pack, or dispenser together with instructions for administration. Typically, an oral dose is taken two- to four-times daily, until symptom relief is apparent. By way of example, an effective amount of the DDM-HCA-containing composition of the invention sufficient for achieving a therapeutic or prophylactic effect will typically range from about 0.000001 mg/Kg body weight/day to about 10,000 mg/Kg body weight/day. Preferably, the dosage ranges are from about 0.0001 mg/Kg body weight/day to about 100 mg/Kg body weight/day. The DDM-HCA compositions of the invention can also be administered in combinations of HCA species alone, or with one or more additional therapeutic compounds, also referred to as "second agents".

II. General

It is to be appreciated that certain aspects, modes, embodiments, variations and features of the invention are described below in various levels of detail in order to provide a substantial understanding of the present invention. In general, such disclosure provides beneficial HCA-containing compositions, combinations of such compositions with other dietary supplement compositions, and related methods of producing and using same.

It is an object of the present invention to provide dimeric double metal salts of group IA and IIA of HCA. DDM-HCAs of the invention are soluble HCA-containing compositions useful as oral dietary supplements. The DDM-HCAs of the invention are suitable for manipulations under those conditions necessary for tabletting, encapsulation, and the production of controlled-release vehicles that can be incorporated into dry powders. It is also an object of the invention to provide methods to make DDM-HCAs of the invention. The methods of the invention are useful to alter the polar/ionic qualities of HCA salts and derivatives when presented to the intestinal lumen to provide advantages in absorption when administered to a subject. It is an object of the present invention to provide DDM-HCAs useful in prophylactic and therapeutic applications in a variety of disorders, diseases and conditions in a subject including merely by way of example, obesity, overweight, hunger, deficiencies in fat metabolism, hyperlipemia, and postprandial lipemia.

III. DDM-HCAs of the Invention

The invention provides new DDM-HCAs of the three (3) general formulas per Table 1, and as described above. In one embodiment, the DDM-HCA of the invention is an isolated DDM-HCA of a general Formula of Formula I, Formula II, or Formula III, as described above. In one embodiment, the DDM-HCA of the invention is a mixture of two or more DDM-HCAs of the general formulas selected from the group consisting of: Formula 1; Formula II; or Formula III, as detailed above. The invention provides that the DDM-HCA may include any combination of dimeric species as well as group IA metals and group IIA metals. In one embodiment, the relative molar ratio of IIA group metal to IA group metal is from at least about 1.0:4.0 to at least about 1.0:4.5. In one embodiment, the DDM-HCA is an HCA-containing composition wherein the group IIA metal is magnesium metal, the group IA metal is potassium metal and the relative molar ratio of magnesium metal to potassium metal is from at least about 1:3.5 to at least about 1:4.5. The DDM-HCAs of general Formula I, Formula II and Formula III, as described above, may be present in the compositions of the invention in any relative molar ratio or combination.

IV. Preparing DDM-HCAs of the Invention

The invention provides process for preparing DDM-HCAs of Formulas I, II, and III, as shown in Table 1 and described above, is schematically represented in FIG. 1. The DDM-HCAs are prepared from a concentrated aqueous extract of the fruit (or rind) of a plant of the genus *Garcinia* that contains (−)-hydroxycitrate as the free acid as well as the HCA lactone, i.e., an HCA/lactone concentrate mixture. The dried fruit of a plant of the genus *Garcinia* or the rinds of the fruit are a rich source of HCA and, therefore, useful in the preparation of the HCA/lactone concentrate mixture. In some embodiments, dried fruit or dried fruit rind(s) of *Garcinia cambogia* are extracted to derived the HCA/lactone concentrate mixture. In one embodiment, the HCA is extracted from dried *Garcinia* fruit/rind in multiple cycles with DM water in an extractor. For example, an extraction cycle can include the extraction of *Garcinia* fruit/rind for at least about six (6) hours to yield a first *Garcinia* extract and a once-extracted *Garcinia* fruit/rind. The once-extracted *Garcinia* fruit/rind is isolated from the *Garcinia* extract and then re-extracted with fresh DM water in another extraction cycle. In one embodiment, the dried *Garcinia* fruit/rind is subjected to four (4) extraction cycles. Following each extraction cycle, the *Garcinia* extract is filtered. In one embodiment, the *Garcinia* extract is filtered using a sparkler filter; such filters useful in the methods of the invention are of sizes 14-10 (Amar Equipments Pvt. Ltd., Kurla (W), Mumbai, India;). Filtered *Garcinia* extracts from multiple extraction cycles are typically pooled at the end of the HCA extraction process and homogenized prior to further purification. In one embodiment of the invention, a mixing tank having a vertically mounted agitator is employed in the homogenization step. In one embodiment, the filtered and homogenized *Garcinia* extract mixture has from about 5% to about 8% total dissolved solids.

After aqueous HCA extraction, the HCA is purified using ion exchange chromatography and concentrated as generally described by Moffett et al. (U.S. Pat. No. 5,536,516, issued Jul. 16, 1996). In one embodiment, the filtered and homogenized *Garcinia* extract mixture is loaded onto an anion exchange column for adsorption of the HCA onto an anion exchange resin, washing the column with DM water to remove unbound components, and then eluting the HCA free acid from the anion exchange column with 5% (w/w) NaOH solution to yield an anion exchange-purified sodium HCA salt solution. The skilled artisan will recognize that there are many anion exchange resins useful in the method of the present invention, including, by way of illustrative examples, anion A.36 gel exchange resin and Indion 850 anion exchange resin, commercially available from Thermax, Ltd, India and Ion Exchange India Ltd., India, respectively. The sodium HCA salt solution is then rendered as the HCA free acid by cation exchange chromatography. In one embodiment, the sodium HCA salt solution is rendered as the HCA free acid by loading it onto a cation exchange column that has been activated with 30% (w/w) HCl. The HCA free acid is collected in the eluant from pH 2.5 to 1.2 and from 1.2 to 2.5. The HCA free acid-containing solution is then bleached (i.e., decolorized) by mixing it with activated charcoal for 1 hour at 80° C. to yield a bleached HCA solution. The bleached solution is allowed to cool to room temperature, filtered, and then loaded onto a cation exchange column to reduce the cation concentration (e.g., Na concentration) to yield an HCA concentrate with at least about 1.0% weight HCA concentration.

The skilled artisan will recognize that there are many commercially available cation exchange resins useful in the method of the present invention including, e.g., Indion 225 H cation exchange resin (Ion Exchange India Ltd., India). The HCA solution is passed through an anion exchange column to reduce the chloride content below 1.0% of the weight of the HCA concentration. In one embodiment, the HCA concentrate has at least about 2.0% weight HCA concentration. While any anion exchange resin, e.g., anion A.36 gel exchange resin (Thermax Ltd., India), suitable to reduce the chloride content of the HCA solution to at least about 1% weight of the HCA concentration are useful in the method of the invention. The HCA concentrate undergoes an aging process as the HCA free acid will lactonize to an equilibrium that is dependent on the pH and concentration. In one embodiment, the HCA concentrate lactonizes to yield the liquid HCA/lactone concentrate mixture wherein the HCA lactone is present at a concentration of least about 20% weight percent of the total weight of the liquid HCA/lactone concentrate mixture.

As detailed in FIG. 1, the HCA/lactone concentrate mixture is partially neutralized, 2 molar equivalents of the liquid HCA/lactone concentrate mixture with 4 molar equivalents of a group IA metal hydroxide. The group IA metal hydroxide solution is slowly added with mixing to the liquid HCA/lactone concentrate mixture under conditions wherein the reaction temperature is maintained from at least about 27° C. to at least about 33° C. to yield a partially neutralized liquid HCA/lactone concentrate mixture. Group IA metal hydroxides useful in the preparation of DDM-HCA include, merely by way of example, LiOH; NaOH; KOH; RbOH; CsOH; and FrOH. In one embodiment, the HCA/lactone concentrate mixture is maintained at least about 30° C. to yield a partially neutralized liquid HCA/lactone concentrate mixture.

After partial neutralization with group IA metal hydroxide, the neutralized liquid HCA/lactone concentrate mixture slowly reacted with mixing with one (1) molar equivalent of a IIA metal hydroxide to yield a fully neutralized liquid HCA/lactone concentrate mixture. Group IIA metal hydroxides useful in the preparation of DDM-HCA include, e.g., $Be(OH)_2$; $Mg(OH)_2$; $Ca(OH)_2$; $Sr(OH)_2$; $Ba(OH)_2$; and $Ra(OH)_2$. The fully neutralized liquid HCA/lactone concentrate mixture is then heated to at least about 60° C. until the pH of the mixture is stable to yield a stabilized DDM-HCA-containing mixture. In one embodiment, the pH of the HCA/lactone concentrate mixture is stabilized to a pH range between about 8.8 and about 9.2. The DDM-HCAs are then isolated from the stabilized DDM-HCA-containing mixture by any suitable separation or processing technique. In one embodiment, the DDM-HCA are isolated from the stabilized DDM-HCA-containing solution by concentrating the stabilized DDM-HCA-containing solution to at least about 25% weight total solids to yield a concentrated DDM-HCA-containing solution. The concentrated DDM-HCA-containing solution is filtered and the DDM-HCA-containing filtrate is dried. In one embodiment, DDM-HCA-containing is dried using spray drying technique.

V. Limitations of Monomeric HCA and HCA Salts

Early work ascribed the weight loss benefit to HCA, its salts and its lactone form; see, for example, U.S. Pat. No. 3,764,692 of Lowenstein. One commonly offered explanation for the biological and therapeutic effects of HCA is the inhibition of cytoplasmic ATP-citrate lyase (D. Clouatre and M. E. Rosenbaum, The Diet and Health Benefits of HCA (Hydroxycitric Acid), 1994). The use of free HCA concentrate in food products has been described in U.S. Pat. No. 5,536,516 of Moffett, issued Jul. 16, 1996, but it does not teach any particular advantage for the use of HCA in weight loss or for other medicinal purposes. Even brief exposure of the potassium and sodium salts of HCA to acidic conditions or flavored beverages results in chemical changes in these HCA salts. In some cases the beverages actually change color upon addition of potassium HCA or sodium HCA salts.

Free HCA is extremely ionic and does not pass readily through the membrane lining the gut. The free acid form of HCA can be sequestered by binding to soluble and insoluble fibers as well as by many other compounds, thus rendering HCA biologically unavailable. Generally, calcium HCA and magnesium HCA salts, either alone or in the form of various mixtures together, or in combination with the potassium HCA and sodium HCA salts, are not biologically effective delivery forms for HCA. Calcium HCA and magnesium HCA salts are also not readily absorbed across the gastrointestinal tract because they are poorly soluble in aqueous media. These HCA salts are also reactive with bile acids and fats in the gut and/or are sequestered by binding to soluble and insoluble fibers or other substances in the diet, and are secreted during digestion (Heymsfield, Steven B, et al. JAMA 1998; 280(18): 1596-1600; Letters, JAMA 1999; 282: 235). For example, the action of stomach acid may free one of the two valences of calcium HCA or magnesium HCA salts for attachment to, e.g., fats, bile acids, gums, fibers, pectins, which is undesirable for biological availability. The addition of a small amount of magnesium HCA to potassium HCA, however, improves the transit of potassium HCA across cell membranes. By contrast, calcium, impedes the transit of potassium HCA across cell membranes.

Calcium/potassium HCA (Super CitriMax®) is not well absorbed, as demonstrated by the observation that only 20% of the total dose ingested by fasted subjects was detected (by gas chromatography/mass spectroscopy) in the blood (Loe et al., Anal. Biochem., 2001, 292(1): 148-54). Loe also reported that the absorption of calcium/potassium HCA (Super CitriMax®) peaked 2 hours after administration, and that the compound remained in the blood for more than 9 hours after ingestion (Loe et al., FASEB Journal, 15 4:632, Abs. 501.1, 2001). Eating a meal shortly after taking Super CitriMax® reduced its absorption by about 60%. Moreover, animal trials (see U.S. Pat. No. 6,476,071 of Clouatre, issued Nov. 5, 2002) have further demonstrated that in order for the potassium salt to be maximally effective, the ligand must be fully bound to the HCA with only trivial amounts of contaminants, including other minerals or fibers or sugars.

Calcium HCA salt has some further disadvantages that may limit its therapeutic use. Calcium uptake from the gut is highly regulated and under normal circumstances does not exceed approximately 35% of the total amount present in foods and supplements. The uptake of calcium declines as the dosage of calcium is increased. This may limit the use of calcium HCA where large doses may need to be ingested. For example, for weight loss and other purposes, a minimally effective amount of HCA derived from its calcium salt requires the administration of between 12 and 15 grams of a 50% (−)-HCA material. This amount of calcium HCA may lead to undesirably elevated levels of binding and excretion of other dietary minerals, such as zinc, aside from presenting difficulties in administration.

HCA sodium salt has disadvantages for long-term administration to a subject. First, sodium HCA lacks positive metabolic effects with regard to obesity. Second, sodium HCA has potential hypertensive actions. Indeed, several of the "potassium" salts in the early commercial products from India were, in fact, mixtures of calcium, potassium and sodium HCA. The amount of sodium in these HCA preparations exceeded that allowed in low sodium diets notwithstanding the fact that any additional sodium is ill-advised in any modern diet. In contrast, potassium HCA does not possess the disadvantages associated with sodium HCA.

A preferred salt of HCA for pharmaceutical use is potassium HCA. The mineral potassium is fully soluble, as is its HCA salt, and is known to possess cell membrane permeability which is 100 times greater than that possessed by sodium. However, the potassium salt of HCA, as is also true of the sodium salt, is extremely hygroscopic and thus is not suitable under normal circumstances for the production of dry delivery forms. In drawing moisture to itself, potassium HCA will also tend to bind to available binding sites of compounds in its immediate environment, and this action often later will markedly impede the assimilation of potassium HCA from the gut.

Several international patent applications and U.S. patents disclose HCA-containing compositions and their delivery as calcium, magnesium, and potassium, and admixtures of salts. International patent application WO 99/03464, filed 28 Jan. 1999, is directed to HCA-containing compositions with 14 to 26 wt % calcium HCA, and approximately 24 to 40 wt % potassium HCA or approximately 14 to 24 wt % sodium HCA, or a mixture thereof, each calculated as a percentage of the total HCA content of the composition for use in dietary supplements and food products. Studies assessing such a composition showed that its assimilation is very poor even when taken on an empty stomach (Loe et al., Anal Biochem. 2001 May 1; 292(1): 148-54), and that eating a meal shortly after taking it reduced its absorption by about 60% (Loe et al., Time Course of Hydroxycitrate Clearance in Fasting and Fed Humans, FASEB Journal, 15, 4: 632, Abs. 501.1, 2001). Further, studies comparing the effect of various HCA-containing compositions on body weight and food intake in a rat obesity model showed that a test composition of calcium/potassium HCA salt identical to that described by WO 99/03464 was inferior compared to potassium HCA salt in its ability to reduce weight gain in middle-aged rats fed a 30% fat diet (see U.S. Pat. No. 6,476,071 of Clouatre). Specifically, at the level of intake used experimentally on a 30% fat diet, potassium HCA increased protein as a percentage of body weight while reducing fat as a percentage of body weight. In contrast, the calcium/potassium salt HCA test composition increased fat and reduced protein as percentages of body weight.

International patent application WO 00/15051 is directed to a method of making calcium HCA more soluble by underreacting the material, i.e., leaving a substantial amount of HCA lactone in the finished product. Making calcium soluble, again, does nothing to prevent its reactivity with compounds in the gut, e.g., bile salts, or to improve the general rate of assimilation of calcium HCA.

U.S. Pat. No. 6,221,901 of Shrivastava, issued Apr. 24, 2001, is directed to the preparation and uses of magnesium HCA. The high dosage of magnesium HCA required to achieve the indicated results, however, may limit the therapeutic utility of the composition. For example, in order to achieve a hypotensive effect, for instance, the inventors fed their animals 500 mg/kg magnesium HCA. Using the standard 5:1 multiplier for rat to human data, the dose of magnesium hydroxycitrate employed by Shrivastava is equivalent to a human ingesting 100 mg/kg/day or 7 grams for the average-sized human subject. Of this amount, 15% would be elemental magnesium; hence we have the equivalent of a human ingesting approximately 1 gram of magnesium. The Recommended Dietary Allowances, 10th edition (National Research Council, 1989), indicates that most humans begin to suffer diarrhea at more than 350 mg/day. In other words, the test dose used by Shrivastava is 3 times the dose at which side effects would normally be expected to begin to appear, and as a further complication, the induced diarrhea itself would lower blood pressure rapidly.

VI. The Chemical and Pharmacokinetic Characteristics of DDM-HCAs of the Invention are Different than Those of Monomeric HCAs DDM-HCA was characterized for select physicochemical properties using an exemplary HCA monomer preparation and DDM-HCA preparation each containing potassium IA group metal and magnesium IIA group metal and prepared as detailed in Example 1, infra. The predicted general Formula IV of the HCA monomer preparation (termed, "K/Mg-HCA monomer") is shown below:

Formula IV

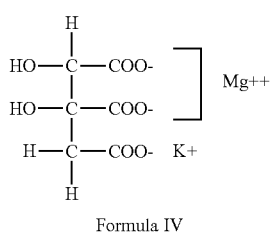

Formula IV

This structure is like the soluble double metal HCA salts disclosed by Balasubramanyam et al., (U.S. Pat. No. 6,160, 172, issued Dec. 12, 2000; U.S. Pat. No. 6,395,296, issued May 28, 2002). The above structured HCA species was used in a kinetic study, comparing it to the dimer, and found to be less-absorbed.

The exemplary DDM-HCA (termed, "K/Mg-DDM-HCA") was a mixture of one or more of the DDM-HCAs of general Formulas V, VII, and VII shown below:

Formulas V, VI, and VII

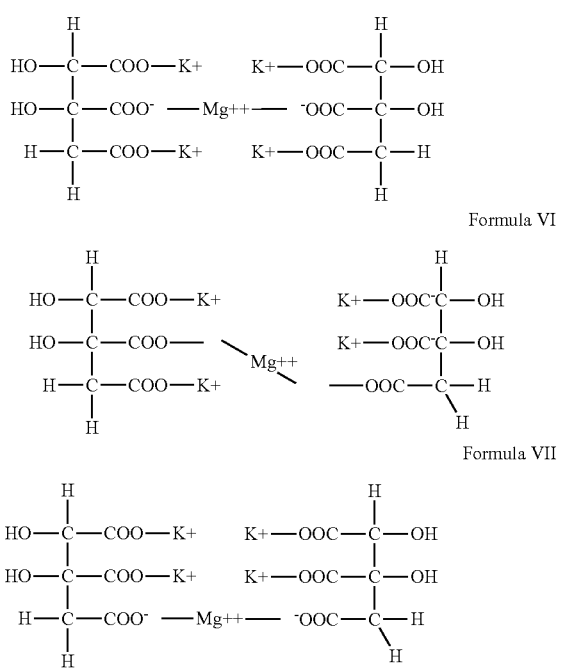

The three carboxylic acid groups of HCA differ in acidity. As such, the three carboxylic acid groups differ in their reactivity with group IA and group IIA metal hydroxides. In this regards, it is known that the primary carboxylic acid group (top) of HCA is the most reactive and the tertiary carboxylic acid group (bottom) is the least reactive. The secondary carboxylic acid group of HCA (middle) is less than the primary carboxylic group of HCA but more reactive than the tertiary carboxylic acid group of HCA. As only two molar equivalent of group 1A metal hydroxide, e.g., KOH, is added to partially neutralize the concentrated HCA/lactone mixture, only two carboxylic acid groups, it is predicted that the top two carboxylic acid groups react with the group IA metal hydroxide (see FIG. 1). The acidity difference between the secondary HCA carboxylic acid and the tertiary HCA carboxylic acid is small, therefore, it is predicted that the group IA metal hydroxide, e.g., KOH, may also react with the tertiary HCA carboxylic acid group in case of free acid only, but not the lactone.

The invention provides methods to prepare DDM-HCAs of reproducible chemical composition as judged by the relative molar ratio of IA group metal to HCA to IIA group metal. For example, as summarized in Table 2, the process for making the DDM-HCAs of the invention yielded K/Mg-DDM-HCA preparations with reproducible relative molar ratios of IIA group metal, HCA, and IA group metal. As shown in Table 2, there was little variation in the relative molar ratios of magnesium to HCA to potassium among the K/Mg-DDM-HCA preparation 1, preparation 2 and preparation 3.

TABLE 2

HCA Preparations and Relative Mg and K Molar Ratios

| Composition | Relative Molar Ratio | | |
|---|---|---|---|
| HCA Preparation | Magnesium | HCA | Potassium |
| Predicted K/Mg-DDM-HCA | 1 | 2 | 4 |
| K/Mg-DDM-HCA Prep 1 | 1.02 | 2.03 | 4 |
| K/Mg-DDM-HCA Prep 2 | 1.02 | 2.02 | 4 |
| K/Mg-DDM-HCA Prep 3 | 1.01 | 2.02 | 4 |
| Predicted K/Mg HCA Monomer | 1 | 1 | 1 |
| K/Mg-HCA monomer | 0.98 | 1 | 1 |

The invention provides methods to prepare DDM-HCAs which are distinct from monomeric HCA preparation. As shown in Table 2, the observed stoichiometry of the group IIA metal, the HCA and group IA metal in K/Mg-DDM-HCA preparations 1-3, was consistent with the predicted stoichiometry, i.e., 1:2:4, DDM-HCAs of Formula V, Formula VI and Formula VII (detailed above, in Table 1). In contrast, the observed stoichiometry of the group IIA metal, HCA and group IA metal in K/Mg-DDM-HCA preparations 1-3, was different than the predicted stoichiometry, i.e., 1:1:1, of K/Mg HCA monomer. Indeed, K/Mg-HCA monomer had a stoichiometry consistent with the monomeric structure of Formula IV as recently described by Balasubramanyam et al., (U.S. Pat. No. 6,160,172, issued Dec. 12, 2000; U.S. Pat. No. 6,395, 296, issued May 28, 2002).

The molecular weight of the DDM-HCAs of the present invention is consistent with the dimeric structure and general Formulas I-III. For example, the molecular weight of the K/Mg-DDM-HCA prepared as described in Example 1 was experimentally determined (Dhanvantari Botanicals Pvt. Ltd Bangalore, India; lot No. L 2407067). Briefly, the percentage of group I A and II A metals were estimated by flame photometry and HCA was estimated by HPLC. The molecular weight of the DDM-HCA was calculated from atomic mass of the DDM-HCA constituents, their stoichiometry and the experimentally estimated percentages. Indeed, the observed molecular weight of the K/Mg-DDM-HCA (MW=594.1 g/mol) was consistent with the predicted molecular weight (MW=590.7 g/mol) for dimeric double metal salts of HCA having in the general Formulas V-VII as these values fell within the experimental error of the molecular weight determination technique. The observed molecular weight of the K/Mg-DDM-HCA prepared by the process of the invention was different than the predicted molecular weight of K/Mg-HCA monomer of general Formula IV (Mw=268.3 g/mol) as recently described by Balasubramanyam et al., in U.S. Pat. No. 6,395,296 issued on May 28, 2002.

The invention provides methods to prepare DDM-HCAs which are physicochemically distinct from monomeric HCA preparation. The melting point is the temperature at which the crystal structure of a solid breaks down with increasing entropy (degree of disorder). For example, the melting point of the K/Mg-DDM-HCA and K/Mg-HCA monomer prepared as described in Example 1 was experimentally determined (Dhanvantari Botanicals Lab, India) using a melting point apparatus, manufactured by Scientific Engineering Corp., Delhi, India. As summarized in Table 3, the process for making the DDM-HCAs of the invention yielded K/Mg-DDM-HCA preparations with a melting point (202° C.) lower than the melting point of the K/Mg-HCA monomer (>350° C.). This observation is consistent with the K/Mg-DDM-HCA preparation and K/Mg-HCA monomer having distinct crystalline structural characteristics.

TABLE 3

HCA Preparations and Chemical Properties

| HCA Preparation | Melting Point | Properties Alcohol Solubility (50% v/v alcohol; 1% wt test) | Aqueous Solubility |
|---|---|---|---|
| K/Mg-DDM-HCA | 202° C. | 90% | 1000 g/liter |
| K/Mg-HCA monomer | >350° C. | 40% | 250 g/liter |

As noted above, the limitations of HCA and HCA salts with regard to solubility have been addressed by the present invention. The process for making the DDM-HCAs of the invention yielded K/Mg-DDM-HCA preparation with solubility properties different from K/Mg-DDM-HCA preparation. As summarized in Table 3, the solubility of the K/Mg-DDM-HCA of the invention (90%) was more than 2-fold greater than the solubility of K/Mg-HCA monomer (40% w/w) when tested at 1% weight in 50% (v/v) ethanol solution. Also, the aqueous solubility of the K/Mg-DDM-HCA of the invention (1000g/liter) was at least about 4-fold greater than the aqueous solubility of the K/Mg-HCA monomer (250 g/liter).

VII. DDM-HCA-Containing Formulations

The DDM-HCAs of the invention are suitable for manipulations under those conditions necessary for tabletting, encapsulation, and the production of controlled-release vehicles that can be incorporated into dry powders. The present invention provides for the use of DDM-HCA of the invention to modulate, e.g., increase or decrease, the delivery of salts and derivatives of HCA. In one embodiment, at least one DDM-HCA is mixed with one or more HCA monomers at a concentration sufficient to modulate, i.e., increase or decrease, the rate of delivery of salts and derivatives of HCA to a subject, compared to the rate of delivery of salts and derivatives of HCA observed in the absence of the DDM-HCA of the invention. The rate of the delivery of salts and derivatives of HCA can be determined as the rate of appearance of HCA ion the serum of a subject. (See Determination of the Pharmacokinetics or Biological Effect of the HCA-containing compositions, infra). The HCA monomer can include, but is not limited to, e.g., HCA free acid, HCA salts, HCA derivatives, or any combination thereof.

As noted above, the potassium salt of HCA may be more efficacious than the sodium salt of HCA for use as an agent for human weight loss, and for other pharmaceutical and/or nutraceutical purposes. The potassium and the sodium salts of HCA, however, present very similar difficulties in handling and manipulation. Potassium HCA is extremely hygroscopic and binds atmospheric water to form a non-palatable paste, which is not suitable for use in tablets, capsules, or powders. This material can be admixed with orange juice or water, but it still requires vacuum pouch sealing under a humidity-controlled atmosphere, and, as such, is inconvenient patient use. Potassium HCA is also reactive with a large number of compounds (tannins, gums, fibers, pectins, etc.) and thereby readily suffers large losses in pharmacological availability.

In some embodiments of the invention, the aforementioned DDM-HCA-containing compositions have a chloride content, measured as halogen content, of less than about 2.9% by weight. In other embodiments, the DDM-HCA-containing compositions have a chloride content, as measured by ion chromatography, of less than about 2.5% weight. In other particular embodiments, the DDM-HCA-containing compositions have a chloride content of less than about 1.0% weight, and in still more particular embodiments, the DDM-HCA-containing compositions have a chloride content of less than about 0.6% weight, as measured by ion chromatography.

In one embodiment, the DDM-HCAs of the invention are included in a dry delivery system, e.g., tablet, dry powder, and dry meal replacement mixture. In another embodiment, the DDM-HCAs of the invention are included in a liquid delivery system, e.g., capsule, caplet, or beverage. In yet another embodiment, the DDM-HCAs of the invention are used in controlled-release vehicles, e.g., tablet, caplet, and capsules.

DDM-HCA compositions of the invention are useful as a granulate which can be used alone or further formulated with pharmaceutically acceptable compounds, excipients, vehicles, or adjuvants with a favorable delivery profile, i.e., suitable for delivery to a subject. Such compositions typically comprise the DDM-HCA composition of the invention and a pharmaceutically acceptable carrier. As used herein, "pharmaceutically acceptable carrier" is intended to include any and all solvents, dispersion media, coatings, antibacterial and antifungal compounds, isotonic and absorption delaying compounds, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. The pH can be adjusted with acids or bases, such as hydrochloric acid or sodium hydroxide.

Oral compositions generally include an inert diluent or an edible carrier. They can be enclosed in gelatin capsules, caplets or compressed into tablets. For the purpose of oral therapeutic administration, the DDM-HCA composition of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature:

a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

The DDM-HCA composition of the invention can also be prepared as pharmaceutical compositions in the form of suppositories (e.g., with conventional suppository bases such as cocoa butter and other glycerides) or retention enemas for rectal delivery.

The various pharmaceutical compositions described above can be included in a container, pack, or dispenser, each together with instructions for administration.

As noted above, it is advantageous to formulate the DDM-HCA-containing compositions of the invention in dosage unit form for ease of administration and uniformity of dosage. The specification for the dosage unit forms of the invention are dictated by and directly dependent on the unique characteristics of the DDM-HCA composition and the particular therapeutic effect to be achieved, and the limitations inherent in the art of compounding such an active compound for the treatment of individuals.

VIII. Uses of the DDM-HCAs of the Invention

A. Prophylactic and Therapeutic Uses of the DDM-HCAs

The DDM-HCAs of the present invention are useful in prophylactic and therapeutic applications in a variety of disorders, diseases and conditions in a subject including, but not limited to, e.g., obesity, overweight, hunger, deficiencies in fat metabolism, hyperlipemia, and postprandial lipemia (i.e., the level of lipids in the blood following a meal). By way of non-limiting example, the compositions of the invention will have efficacy for treatment of subjects suffering from the mentioned disorders mentioned in the section on Indicated Diseases and Disorders, infra.

B. Determination of the Pharmacokinetics or Biological Effect of the HCA-containing Compositions The pharmacokinetics of DDM-HCA compositions, including absorption, can be determined by measuring the HCA level in the blood of subjects administered an DDM-HCA composition using gas chromatography/mass spectroscopy (Loe et al., Anal Biochem. 2001, 1;292(1):148-54) and as further detailed by Loe et al., (FASEB Journal, 2001, 15 4:632, Abs. 501.1). The assessment and comparison of the pharmacokinetics of test compounds is well known in the art.

The effect of DDM-HCA compositions on the activity of ATP-citrate lyase can be measured using the ATP-citrate lyase assay procedure as detailed by Houston and Nimmo (Biochim Biophys Acta 1985 Feb. 21; 844(2): 233-9). A reduction in ATP-citrate lyase activity in the presence of DDM-HCA composition when compared to the level of ATP-citrate lyase activity observed in the absence of DDM-HCA composition indicates that the DDM-HCA composition inhibits ATP-citrate lyase enzyme.

In various embodiments of the invention, suitable in vitro or in vivo assays are performed to determine the effect of a specific HCA-based therapeutic and whether its administration is indicated for treatment of the affected tissue in a subject.

In various specific embodiments, in vitro assays can be performed with representative cells of the type(s) involved in the patient's disorder, to determine if a given HCA-based therapeutic exerts the desired effect upon the cell type(s). Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

C. Indicated Diseases, Disorders, and Conditions

The invention provides for both prophylactic and therapeutic methods of treating a subject at risk of (or susceptible to) a disease or having a disorder associated with lipid metabolism, e.g., but not limited to, obesity, overweight, deficiencies in lipid metabolism, hyperlipemia, postprandial lipemia, disorders where inhibition of inhibit cytoplasmic citrate lyase is advantageous, or physical conditions such as hunger.

The DDM-HCA compositions of the present invention are useful prevent or treat diseases, disorders or conditions where inhibition of inhibition of ATP-citrate lyase is advantageous, e.g., reduction of cholesterol level. Berkhout et al., (Biochem J. 1990 Nov. 15; 272(1): 181-6) studied the effect of HCA on the activity of the low-density lipoprotein receptor and 3-hydroxy-3-methylglutaryl-CoA reductase levels in the human hepatoma cell line Hep G2. After 2.5 h and 18 h incubations with HCA at concentrations of 0.5 mM or higher, incorporation of [1,5-14C]citrate into fatty acids and cholesterol was strongly inhibited. It was concluded that this decrease reflected an effective inhibition of ATP citrate-lyase. Cholesterol biosynthesis was decreased to 27% of the control value as measured by incorporation of tritium from tritiated water, indicating a decreased flux of carbon units through the cholesterol-synthetic pathway. The DDM-HCA compositions of the invention are useful, therefore, to prevent or treat diseases, disorders or conditions where inhibition of inhibition of ATP-citrate lyase is advantageous, e.g., reduction of cholesterol level.

The DDM-HCA compositions of the present invention are useful to prevent or treat diseases or disorders associated with lipid metabolism, e.g., but not limited to, obesity; overweight; hyperlipemia; postprandial lipemia; and deficiencies in lipid metabolism, e.g., insulin resistance. Ishihara et al., (J Nutr. 2000 December; 130(12): 2990-5) studied the effect of chronic HCA administration on both carbohydrate utilization and lipid oxidation. The respiratory exchange ratio of test subjects was significantly lower in the HCA group during both resting and exercising conditions. These results suggest that chronic administration of HCA promotes lipid oxidation and spares carbohydrate utilization in test subjects at rest and during running. The DDM-HCA compositions of the present invention are useful, therefore, to prevent or treat diseases or disorders associated with lipid metabolism, e.g., but not limited to, obesity; overweight; hyperlipemia; postprandial lipemia; and deficiencies in lipid metabolism, e.g., insulin resistance.

Under conditions that elevate de novo lipogenesis in humans, HCA reduced fat synthesis and increased energy expenditure (Kovacs and Westerp-Plantenga, Society for the Study of Ingestive Behavior, Annual Meeting, 2001, Abstr. pg. 27). The DDM-HCA compositions of the present invention are useful, therefore, to prevent or treat diseases or disorders associated with lipid metabolism.

The DDM-HCA compositions of the present invention are useful to prevent or treat hunger and to promote satiety in a subject. The administration of HCA to subjects has been reported to promote appetite suppression and satiety (Westerterp-Plantenga and Kovacs, Int. J. Obes. Relat. Metab. Disord., 2002, 26(6): 870-2). The DDM-HCA compositions of the present invention are useful, therefore, to prevent or treat hunger and to promote satiety in a subject. The disclosures of these references provided in this list immediately above are herein incorporated in their entirety by reference thereto

EXAMPLES OF PREPARATION AND TESTING

Example 1

Preparation of K/Mg-DDM-HCA and K/Mg-HCA Monomer

A. Preparation of K/Mg-DDM-HCA

K/Mg-DDM-HCA was prepared as a mixture of DDM-HCAs of general Formula I; Formula II; and Formula III, as depicted in Table 1 and described above. These structures are further detailed as K/Mg-DDM-HCAs of general Formulas V-VII, supra.

The K/Mg-DDM-HCA was prepared from a concentrated aqueous extract of the rind of the fruit of a plant of the genus *Garcinia* (i.e., *Garcinia* rind) that contains (−)-hydroxycitrate as the free acid as well as HCA lactone, i.e., HCA/lactone concentrate mixture. Specifically, the HCA was extracted from dried *Garcinia* rind in multiple cycles with DM water in an extractor (HR Engineering, Bangalore, India). Specifically, 600 kilograms of dried *Garcinia* rind was extracted in an extractor with 1200 liters of distilled water. The *Garcinia* rind was extracted for six (6) hours to yield a first *Garcinia* extract and a once-extracted *Garcinia* rind. The once-extracted *Garcinia* rind was isolated from the *Garcinia* extract and then re-extracted with three more extraction cycles with fresh DM water as detailed above. Following each extraction cycle, the *Garcinia* extract was filtered using a sparkler filter (Amar Equipments Pvt. Ltd., Kurla (W), Mumbai, India; Size—14-10). Filtered *Garcinia* extracts from multiple extraction cycles were pooled at the end of the HCA extraction process and homogenized prior to further purification in an 8,000 liter mixing tank with a vertical agitator.

After aqueous HCA extraction, the HCA was purified using ion exchange chromatography technique and concentrated as generally described by Moffett et al. (U.S. Pat. No. 5,536,516, issued Jul. 16, 1996). Briefly, a volume of filtered and homogenized *Garcinia* extract mixture with 5% to 8% total dissolved solids, containing equivalent to 150 kg of HCA was loaded at room temperature (i.e., 25-35 °C.) onto an anion exchange column containing 1200 liters Indion 850 anion exchange resin (Ion Exchange India Ltd., India) at a flow of 3000 liters/hr for adsorption of the HCA onto an anion exchange column. Washing the column with DM water to remove unbound components and then the (−)-hydroxycitric acid is eluted from the anion exchange column with 5% w/w NaOH solution to yield an anion exchange purified sodium HCA salt solution. The sodium HCA salt solution was then rendered as the HCA free acid by cation exchange chromatography. Briefly, the sodium HCA salt was rendered as the HCA free acid by loading it at room temperature (i.e., 25-35° C.) onto a cation exchange column containing 1600 liters of Indion 225 H resin (Ion Exchange India Ltd., India) at a flow of 3000 liters/hr that was activated with 30% (w/w) HCl. The pH of the eluant generally stays at pH 2.5 and goes down to pH 1.2 as the concentration of HCA increased. It remained stable for a while and once the HCA concentration started reducing, the pH went back up from pH 1.2 to pH 2.5. As such, the HCA free acid was collected in the eluant from pH 2.5 to 1.2 and from 1.2 to 2.5. The HCA free acid-containing solution was then bleached (i.e., decolorized) by mixing it with activated charcoal (2.0% (w/v) activated charcoal; 60 kg total) for 1 h at 80° C. to yield a bleached HCA solution. The bleached solution was allowed to cool to room temperature, filtered and then loaded onto a cation exchange column with 1000 liters of Indion 225H resin at a flow rate of 3000 liter/hr, to reduce the cation concentration, e.g., Na, to yield an HCA concentrate with at least about 2.0% weight HCA concentration. The HCA solution was passed through an anion exchange column containing 60 liters of anion A.36 gel exchange resin (Thermax, Ltd., India) at a flow rate of 1600 liters/hr to reduce the chloride content below 1.0% of the HCA concentration. The HCA concentrate undergoes an aging process as the HCA free acid will lactonize to an equilibrium which was dependent upon the pH and concentration. The HCA concentrate lactonized to yield the liquid HON lactone concentrate mixture wherein the HCA lactone was present at a concentration of least about 25% weight percent of the total weight of the liquid HCA/lactone concentrate mixture.

A volume of the 2% weight HCA/lactone concentrate mixture equal to 50 kg equivalents of HCA was partially neutralized (2 molar equivalents of the liquid HCA/lactone concentrate mixture) with 4 molar equivalents of a potassium hydroxide solution at 30% weight concentration. The potassium hydroxide solution was slowly added with mixing to the liquid HCA/lactone concentrate mixture under conditions wherein the reaction temperature was maintained at least about 30° C. to yield a partially neutralized liquid HCA/lactone concentrate mixture.

After partial neutralization with potassium hydroxide, the partially neutralized liquid HCA/lactone concentrate mixture was slowly reacted (with mixing) with one (1) molar equivalent of magnesium hydroxide as a 10% (w/v) solution of the group IIA metal hydroxide to yield a fully neutralized liquid HCA/lactone concentrate mixture. The fully neutralized liquid HCA/lactone concentrate mixture was then heated to about 60° C. until the pH of the mixture was stable between pH 8.8-9.2, to yield a stabilized K/Mg-DDM-HCA-containing mixture. The K/Mg-DDM-HCAs were then isolated from the stabilized K/Mg-DDM-HCA-containing mixture by concentrating the stabilized K/Mg-DDM-HCA-containing solution to about 25% weight total solids to yield a concentrated K/Mg-DDM-HCA-containing solution. The concentrate was stored in a storage tank prior to spray drying. The concentrated K/Mg-DDM-HCA-containing solution was filtered and the K/Mg-DDM-HCA-containing filtrate was dried using spray drying technique.

B. Preparation of K/Mg-HCA Monomer

K/Mg-HCA monomer having the general Formula IV, supra, was prepared as described below. The K/Mg-HCA was prepared from a concentrated aqueous extract of the fruit of a plant of the genus *Garcinia* that contained (−)-hydroxycitrate as the free acid as well as HCA lactone, i.e., HCA/lactone concentrate mixture prepared as a 2% weight HCA/lactone concentrate mixture as detailed above in Section A of this Example.

A volume of the 2% weight HCA/lactone concentrate mixture equal to 50 kg equivalents of HCA was partially neutralized with 1 molar equivalent of the liquid HCA/lactone concentrate mixture with 1 molar equivalent of a magnesium hydroxide. The magnesium hydroxide was slowly added as a 10% (w/w) solution with mixing to the liquid HCA/lactone concentrate mixture under conditions wherein the reaction temperature was maintained at least about 30° C. to yield a partially neutralized liquid HCA/lactone concentrate mixture.

After partial neutralization with magnesium hydroxide, the liquid HCA/lactone concentrate mixture was slowly reacted (with mixing) with one (1) molar equivalent of potassium hydroxide as a 30% w/w solution of the group IA metal hydroxide to yield a fully neutralized liquid HCA/lactone concentrate mixture. The fully neutralized liquid HCA/lactone concentrate mixture was then heated to about 60° C. until the pH of the mixture was stable between pH 8.8 and pH 9.2 to yield a stabilized K/Mg-HCA monomer preparation. The K/Mg-HCA monomer was then isolated from the stabilized K/Mg-HCA monomer preparation by concentrating the stabilized K/Mg-HCA monomer preparation to about 25% weight total solids to yield a concentrated K/Mg-HCA monomer solution. The concentrate was stored in a storage tank prior to drying. The concentrated K/Mg-HCA monomer solution was filtered and the K/Mg-HCA monomer-containing filtrate was dried using spray drying technique.

Example 2

Comparison of Oral HCA Compositions Regarding Serum Plasma Bioavailability in a Rabbit Study An independent study conducted by a third party, using a validated method for quantification of HCA (developed by Balint Analytical Laboratory, Budapest, Hungary) compared the levels of HCA in the serum of New Zealand white rabbits in response to oral gavage with two HCA preparations at a dose of 50 mg/kg body weight: (1) a preparation of the inventive DDM-HCA composition (67.31% HCA (KMg 24.33%/4.02%) and (2) Super Citrimax™ containing potassium-calcium HCA (Interhealth). Thirty minutes after receiving the respective preparations, the group of three rabbits receiving the inventive DDM-HCA preparation had a mean serum HCA level of 11.3 µg/mL, a value 45.8% higher than the 6.13 µg/mL serum value of the group of three rabbits receiving the Super Citrimax™ preparation. These results demonstrate a superior bioavailability of HCA when it is delivered orally in the from of the inventive DDM-HCA composition, as detailed in Table 1.

Example 3

Testing DDM-HCA in a Rat Model

An OM rat model is useful to test the biological properties of the DDM-HCA dosage unit forms of the invention. Briefly, male OM rats aged 10 weeks are fed a diet in which 30% of the calories are obtained from fat under standard conditions. Groups of 5-10 rats are intubated twice daily for 60 days with DDM-HCA dosage unit forms (e.g., 0.01 mmoles/kg body weight to 1 mole/kg body weight equivalent) or vehicle-control solutions with no added DDM-HCA. Blood is withdrawn from the tail vein one or more times daily. The pharmacokinetics of HCA-containing dosage unit form, including absorption, is determined by measuring the HCA level in the blood of subjects administered the HCA-containing dosage unit form using gas chromatography/mass spectroscopy (Loe et al., Anal Biochem. 2001, 1; 292(1): 148-54; and Loe et al., FASEB Journal, 2001, 15 4:632, Abs. 501.1). Body weight of the test subjects as well as, blood levels of lipids, hormones and metabolic indicators are measured; such indicators may include, for example, LDL and HDL, glucocorticoids, leptin, insulin, and corticosterone level (see U.S. Pat. No. 6,482,858 of Clouatre, issued Nov. 19, 2002). Such measurements are taken prior to the DDM-HCA treatment, over the course of the 60 days, and when the animals are sacrificed at the termination of the study. Data from the various experimental and control groups are compared and statistically analyzed using the Students t-test (one- or two-tailed P-values) or ANOVA. A P-value of less than or equal to about 0.05 is considered statistically significant. A statistically significant alteration, e.g., increase or decrease, in an experimental parameter of test subjects receiving DDM-HCA dosage unit form compared to subjects receiving placebo indicates that the DDM-HCA dosage unit form is a form capable of the prevention or treatment of diseases or conditions characterized by alterations in such parameters.

Equivalents of the Invention

While a number of particular embodiments of the invention and variations thereof have been described in detail, other modifications and methods of using the disclosed therapeutic combinations will be apparent to those of skill in the art. Accordingly, it should be understood that various applications, modifications, and substitutions may be made of equivalents without departing from the spirit of the invention or the scope of the claims. Various terms and conventions have been used in the description to convey an understanding of the invention. It will be understood that a corresponding description of these various terms applies to common linguistic or grammatical variations or forms of these various terms. It will also be understood that some compounds have been identified by trade names, but that these names are provided as contemporary examples, and the invention is not limited by such literal scope, particularly when compounds have been described in chemical terms. Although the written description offers biochemical theory and interpretation of available data in describing the invention, it should be understood that such theory and interpretation do not bind or limit the claims. Further, it should be understood that the invention is not limited to the embodiments set forth herein for purposes of exemplification, but is to be defined only by a fair reading of the appended claims, including the full range of equivalency to which each element thereof is entitled.

We claim:

1. A process for preparing a composition comprising at least one dimeric, double metal salts of group IA and group IIA of (−)-hydroxycitric acid selected from the group consisting of: Formula I; Formula II; and Formula III, or any mixture thereof, as given below:

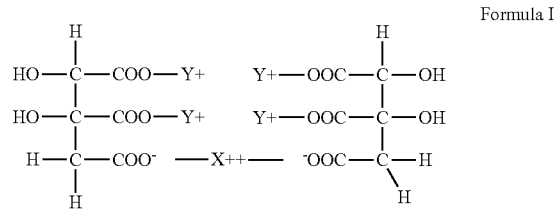

Formula I

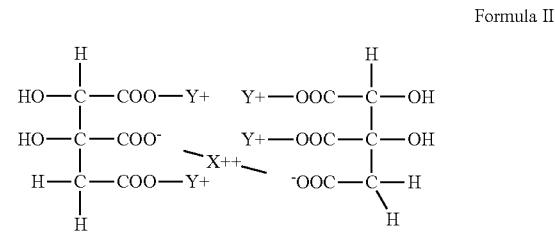

Formula II

-continued

Formula III

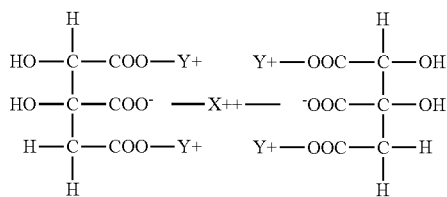

wherein X is IIA group metal: Be, Mg, Ca, Sr, Ba, or Ra;
wherein Y is IA group metal: Li, Na, K, Rb, Cs, or Fr; and
wherein the relative molar ratio of IIA group metal to IA group metal is from at least about 1:3.5 to at least about 1:4.5, comprising the steps of:

a. preparing a liquid (−)-hydroxycitric acid/lactone concentrate mixture;
b. partially neutralizing 2 molar equivalents of the liquid (−)-hydroxycitric acid/ lactone concentrate mixture with 4 molar equivalents of a group IA metal hydroxide under conditions wherein the reaction temperature is maintained from at least about 27° C. to at least about 33° C. to yield a partially neutralized liquid (−)-hydroxycitric acid/lactone concentrate mixture;
c. reacting the partially neutralized liquid (−)-hydroxycitric acid/lactone concentrate mixture of step b with one (1) molar equivalent of a IIA metal hydroxide to yield a fully neutralized liquid (−)-hydroxycitric acid/lactone concentrate mixture;
d. hydrolyzing the lactone component of the fully neutralized liquid (−)-hydroxycitric acid/lactone concentrate mixture of step c by heating the mixture to at least about 60° C. until the pH of the mixture is stable from about pH 8.8 to about pH 9.2 to yield a (−)-hydroxycitric acid dimeric double metal salt solution; and
e. isolating the dimeric, double metal salts of group IA and group IIA of (−)-hydroxycitric acid from the (−)-hydroxycitric acid dimeric, double metal salt solution of step d, thereby preparing the composition comprising at least one dimeric, double metal salts of group IA and group IIA of (−)-hydroxycitric acid selected from the group consisting of: Formula I;

Formula II; and Formula III, or any mixture thereof, as given below:

Formula I

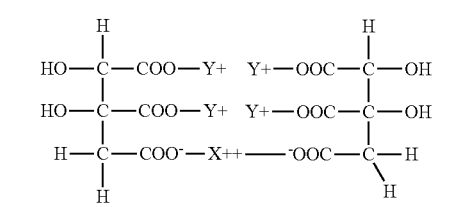

Formula II

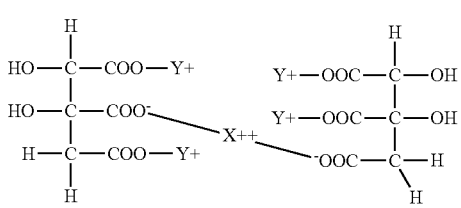

-continued

Formula III

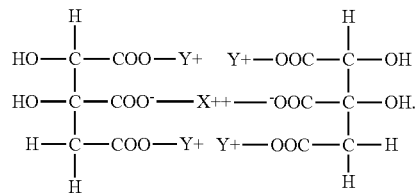

2. The process of claim 1, wherein step A, the preparing a (−)-hydroxycitric acid/lactone concentrate mixture, is by extracting a (−)-hydroxycitric acid/lactone concentrate mixture from dried *Garcinia* rind.

3. The process of claim 2, wherein extracting the (−)-hydroxycitric acid/lactone concentrate mixture comprises the following steps:

a. extracting (−)-hydroxycitric acid from a dried *Garcinia* rind with demineralized water in an extractor for at least about 6 h to yield a first *Garcinia* extract and a once-extracted *Garcinia* rind;
b. filtering the first *Garcinia* extract of step a;
c. extracting the once-extracted *Garcinia* rind of step a with demineralized water in an extractor for at least about 6 h to yield a second *Garcinia* extract and a twice-extracted *Garcinia* rind;
d. filtering the second *Garcinia* extract of c;
e. extracting the twice-extracted *Garcinia* of step c with demineralized water in an extractor for at least about 6 h to yield a third *Garcinia* extract and a three-times-extracted *Garcinia* rind;
f. filtering the third *Garcinia* extract of step e;
g. extracting the three-times-extracted *Garcinia* rind of step e with demineralized water in an extractor for at least about 6 h to yield a fourth *Garcinia* extract and a four-times-extracted *Garcinia* rind;
h. filtering the fourth *Garcinia* extract of step f;
i. combining the filtered *Garcinia* extracts from step b, step d, step f and step h to yield a combined *Garcinia* mixture;
j. homogenizing the combined *Garcinia* extract mixture;
k. loading the homogenized *Garcinia* extract mixture of step j onto an anion exchange column for adsorption of the (−)-hydroxycitric acid onto the anion exchange column for adsorption of the (−)-hydroxycitric acid onto the anion exchange column;
l. eluting the (−)-hydroxycitric acid from the anion exchange column with sodium hydroxide solution to yield an anion exchange purified (−)-hydroxycitric acid sodium salt solution;
m. loading the purified (−)-hydroxycitric acid sodium salt of step I onto a cation exchange column for collection of free (−)-hydroxycitric acid as a free acid in a cation exchange purified (−)-hydroxycitric acid solution;
n. bleaching the cation exchange purified (−)-hydroxycitric acid solution of step m by mixing the cation exchange purified (−)-hydroxycitric acid solution with activated charcoal for 1 h at 80° C. to yield a bleached (−)-hydroxycitric acid solution;
o. cooling the bleached (−)-hydroxycitric acid solution to room temperature;
p. filtering the bleached (−)-hydroxycitric acid;
q. loading the bleached (−)-hydroxycitric acid solution of step p onto a cation exchange column to reduce the cation concentration of the bleached (-r hydroxycitric acid solution;

r. loading the bleached (−)-hydroxycitric acid solution of step q onto an anion exchange column to reduce the chloride concentration of the bleached (−) hydroxycitric acid solution to yield a (−)-hydroxycitric acid concentrate with at least about 1.0 percent weight (−)-hydroxycitric acid concentration; and s. aging the (−)-hydroxycitric acid concentrate of step r to yield the liquid (−) hydroxycitric acid/lactone concentrate mixture;

wherein the liquid (−)-hydroxycitric acid/lactone concentrate mixture wherein the (−)-hydroxycitric acid lactone is present at a concentration of least about 20% weight percent of the total weight of the liquid (−)-hydroxycitric acid/lactone concentrate mixture.

4. The process of claim 1, wherein step e, isolating the dimeric, double metal salts of group IA and group IIA of (−)-hydroxycitric acid from the (−)-hydroxycitric acid dimeric double metal salt solution, comprises the substeps:

1. concentrating the (−)-hydroxycitric acid dimeric, double metal salt solution to at least about 25% weight percent total solids to yield a concentrated (−)-hydroxycitric acid dimeric, double metal salt solution;

2. filtering the concentrated (−)-hydroxycitric acid dimeric, double metal salt solution of step a to yield a filtrate; and 3. drying the filtrate of step b.

5. The process of claim 4, wherein step 3, the drying of the filtrate, is a spray drying.

6. The process of claim 1, wherein the group IA metal hydroxide is selected from the group consisting of: LiOH, NaOH, KOH, RbOH, CsOH, and FrOH.

7. The process of claim 1, wherein the group IIA metal hydroxide is selected from the group consisting of: Be(OH)$_2$, Mg(OH)$_2$, Ca(OH)$_2$, Sr(OH)$_2$, Ba(OH)$_2$, and Ra(OH)$_2$.

* * * * *